US012778640B2

(12) United States Patent
Biedermann et al.

(10) Patent No.: US 12,778,640 B2
(45) Date of Patent: Nov. 3, 2026

(54) COUPLING DEVICE FOR COUPLING A ROD TO A BONE ANCHORING ELEMENT

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 19/421,961

(22) Filed: Dec. 16, 2025

(65) Prior Publication Data

US 2026/0174475 A1 Jun. 25, 2026

Related U.S. Application Data

(60) Provisional application No. 63/737,974, filed on Dec. 23, 2024.

(30) Foreign Application Priority Data

Dec. 23, 2024 (EP) .................................... 24223030
Dec. 9, 2025 (EP) .................................... 25221890

(51) Int. Cl.
*A61B 17/70* (2006.01)
*A61B 17/00* (2006.01)

(52) U.S. Cl.
CPC *A61B 17/7037* (2013.01); *A61B 2017/00526* (2013.01)

(58) Field of Classification Search
CPC ........................................ A61B 17/7035–7038
See application file for complete search history.

(56) References Cited

U.S. PATENT DOCUMENTS 8,696,711 B2 * 4/2014 Jackson ............... A61B 17/702 606/266
9,186,187 B2 11/2015 Mishra
(Continued)

FOREIGN PATENT DOCUMENTS

| | | | |
|---|---|---|---|
| EP | 2 918 236 A1 | | 9/2015 |
| EP | 3 476 340 A1 | | 5/2019 |
| WO | WO 2024/252216 A1 | | 12/2024 |

OTHER PUBLICATIONS

Extended European Search Report for Application No. 24223030.8, dated Jun. 11, 2025, 10 pages.

*Primary Examiner* — Nicholas J Plionis
(74) *Attorney, Agent, or Firm* — Womble Bond Dickinson (US) LLP

(57) ABSTRACT

A coupling device for coupling a rod to a bone anchoring element includes a receiving part having a first end, a second end, an accommodation space for accommodating the head of the bone anchoring element, and an opening at the second end, and a pressure element positionable at least partially in the accommodation space, the pressure element configured to engage the rod and having an expandable portion configured to engage and exert pressure on the head. The pressure element is insertable through the opening into the accommodation space while at a first rotational orientation, and is rotatable to a second rotational orientation to engage a first engagement surface of the receiving part with a second engagement surface of the pressure element to restrict movement of the pressure element towards the first end.

20 Claims, 7 Drawing Sheets

(56) References Cited

U.S. PATENT DOCUMENTS

| | | | | |
|---|---|---|---|---|
| 9,486,246 | B2 | 11/2016 | Biedermann et al. | |
| 10,105,162 | B2 | 10/2018 | Kim | |
| 10,874,438 | B2 | 12/2020 | Biester et al. | |
| 11,331,124 | B2 | 5/2022 | Toon et al. | |
| 11,819,249 | B2 | 11/2023 | Jackson et al. | |
| 12,114,898 | B2 | 10/2024 | McClinktock et al. | |
| 2005/0277928 | A1* | 12/2005 | Boschert ............ | A61B 17/7037 606/328 |
| 2007/0288004 | A1 | 12/2007 | Alvarez | |
| 2010/0152787 | A1 | 6/2010 | Walsh et al. | |
| 2011/0152949 | A1* | 6/2011 | Biedermann ...... | A61B 17/7037 606/305 |
| 2012/0136395 | A1* | 5/2012 | Biedermann ...... | A61B 17/7035 606/279 |
| 2013/0013003 | A1 | 1/2013 | Carbone et al. | |
| 2013/0096621 | A1* | 4/2013 | Biedermann ...... | A61B 17/7037 606/279 |
| 2014/0025119 | A1* | 1/2014 | Biedermann ...... | A61B 17/7032 606/266 |
| 2016/0361095 | A1 | 12/2016 | Burdi et al. | |
| 2019/0183535 | A1 | 6/2019 | May et al. | |

* cited by examiner

COUPLING DEVICE FOR COUPLING A ROD TO A BONE ANCHORING ELEMENT

CROSS-REFERENCE TO RELATED APPLICATION(S)

The present application claims priority to and the benefit of U.S. Provisional Patent Application No. 63/737,974, filed Dec. 23, 2024, the contents of which are hereby incorporated by reference in their entirety, claims priority from European Patent Application EP 24 223 030.8, filed Dec. 23, 2024, the contents of which are hereby incorporated by reference in their entirety, and claims priority from European Patent Application EP 25 221 890.4, filed Dec. 9, 2025, the contents of which are hereby incorporated by reference in their entirety.

BACKGROUND

Field

The present application relates to a coupling device for coupling a rod to a bone anchoring element. In particular, the present application relates to a coupling device that forms part of a polyaxial bone anchoring device.

Description of Related Art

Various types of polyaxial bone anchoring devices are known in the art. Usually, a polyaxial bone anchoring device includes a coupling device and a bone anchoring element with a head that is pivotably received in the coupling device and that can be locked at a desired angle relative to the coupling device. The coupling device also receives a rod that is configured to connect the polyaxial bone anchoring device to a further bone anchor.

For example, U.S. Pat. No. 9,486,246 B2 describes a bone anchoring device that includes an anchoring element including a shaft and a head, a receiving part having a first end and a second end, a channel for receiving a rod near the first end, and an accommodation space for accommodating the head near the second end, and a pressure element configured to be located at least partially in the accommodation space and including a flexible portion to clamp the head. The coupling device may be assembled by inserting the pressure element from the first end into the receiving part at a first rotational orientation, then the pressure element is rotated by 90° such that a projection engages a recessed portion in the receiving part. In this position, the pressure element is prevented from escaping through the first end. The bone anchoring device can be used as a bottom loading polyaxial bone anchoring device, where the bone anchoring element is inserted into the receiving part from the second or bottom end. In an alternative way of assembling, the pressure element is first assembled with the bone anchoring element. Then the bone anchoring element with the pressure element mounted thereon is inserted from the first or top end into the receiving part at a first rotational orientation, and then rotated until the projection of the pressure element engages the recessed portion of the receiving part at a second rotational orientation.

SUMMARY

It is an object of the invention to provide an improved coupling device that can be used with a bone anchoring element having an enlarged head, and a bone anchoring device including such a coupling device and bone anchoring element.

According to an embodiment of the invention, a coupling device for coupling a rod to a bone anchoring element having a head and a shank includes a receiving part having a first end, a second end, a central axis extending between the first end and the second end, a passage extending from the first end to the second end, a recess for receiving the rod, the recess extending the from the first end towards the second end and forming two free legs, and an accommodation space for accommodating the head of the bone anchoring element, the accommodation space having an opening at the second end. The coupling device further includes a pressure element configured to be located at least partially in the accommodation space and having a first portion with a rod support surface and a second portion having a hollow interior with an opening defining a flexible portion configured to accommodate and clamp the head. The receiving part further includes a first securing portion and the pressure element further includes a second securing portion configured to engage the first securing portion The pressure element is insertable into the receiving part from the second end at a first rotational orientation relative to the receiving part where the first securing portion and the second securing portion are out of engagement, and the pressure element is rotatable in the receiving part to assume a second rotational orientation with respect to the receiving part where the first securing portion and the second securing portion are engaged to prevent the pressure element from moving towards the first end.

With such a coupling device, bone anchoring elements with an enlarged head that cannot be inserted through the first or top end of the coupling device can still be used. Instead, the bone anchoring device is designed as a bottom loading bone anchoring device, where the head of the bone anchoring element is inserted into the receiving part from the bottom end thereof.

Due to the design of the coupling device, the overall lateral dimension of the coupling device may be kept small. At the same time, a robust bone anchoring device can be provided due to an increased holding force between the head of the bone anchoring element in the pressure element and the receiving part.

In addition, a maximum pivot angle of the bone anchoring element relative to the receiving part may be increased.

The coupling device and the bone anchoring device including such a coupling device provides a modular arrangement where the desired parts can be selected and assembled in a simple manner at the operation site, or at any other place after the parts have been manufactured. Such a modular bone anchoring device allows for combinations of various anchoring elements with the receiving part on demand, depending on actual clinical requirements and situations. This reduces the cost of the bone anchoring devices, reduces the inventory, and gives the surgeon a substantial and more varied choice of implants.

BRIEF DESCRIPTION OF THE DRAWINGS

Further features and advantages of the invention will become apparent from the description of embodiments by means of the accompanying drawings. In the drawings.

DETAILED DESCRIPTION

Figure 1:
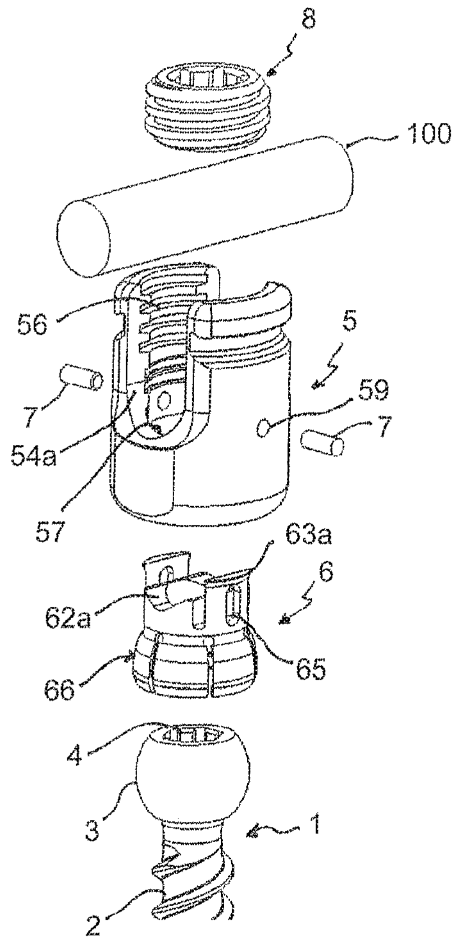
FIG. 1 shows an exploded perspective view of a polyaxial bone anchoring device with a coupling device and a rod according to a first embodiment.
Figure 2:
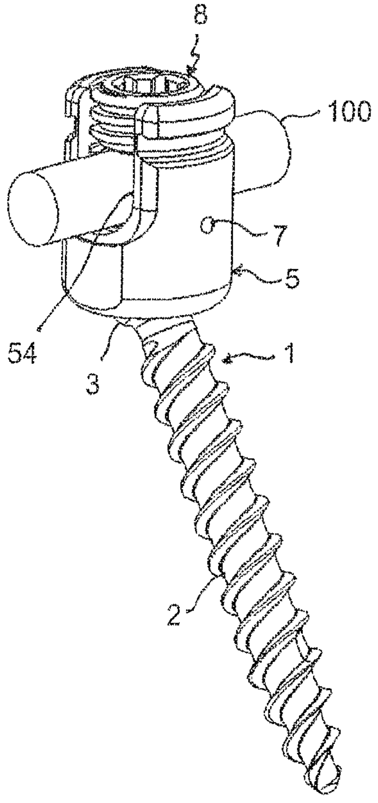
FIG. 2 shows a perspective view of the polyaxial bone anchoring device of FIG. 1 in an assembled state.
Figure 3:
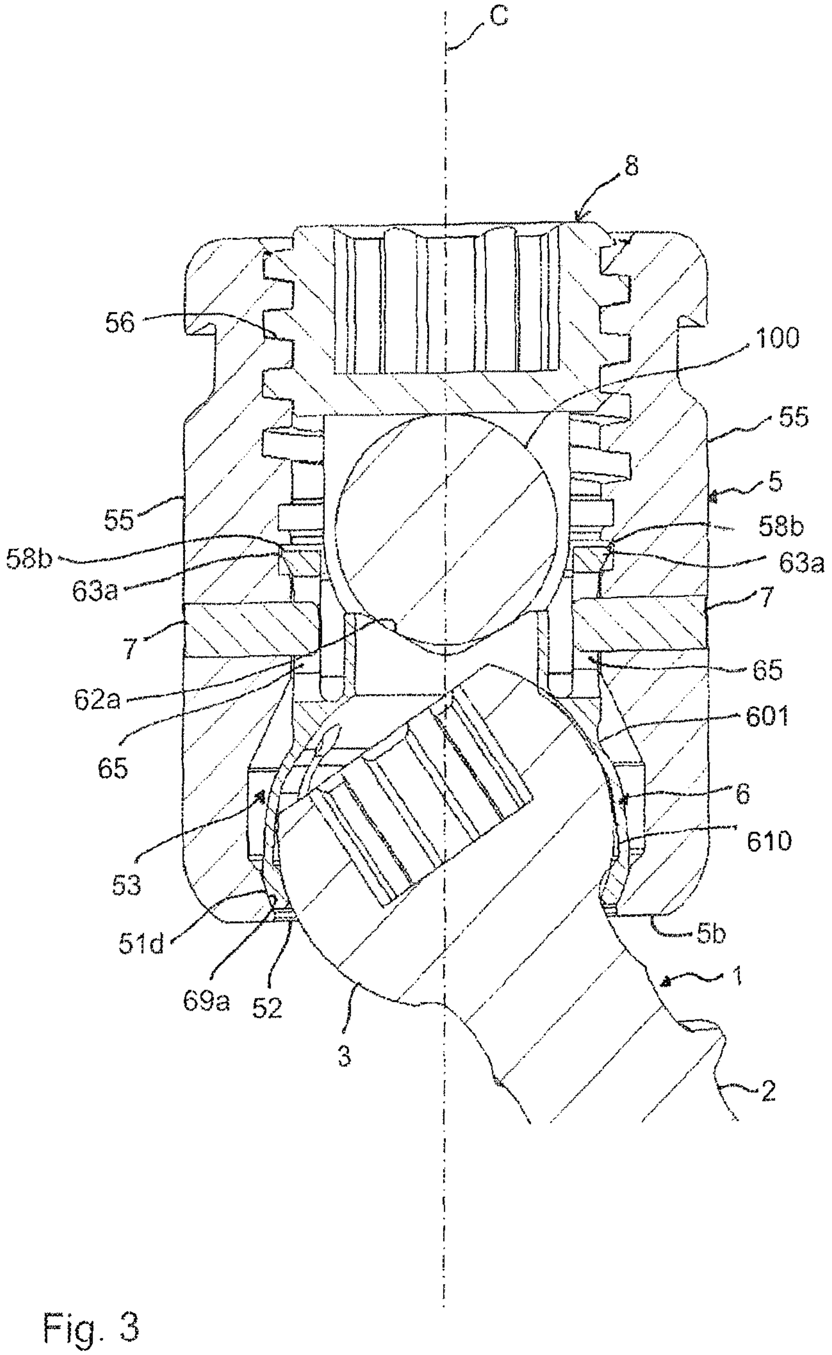
FIG. 3 shows a cross-sectional view of the polyaxial bone anchoring device of FIGS. 1 and 2, the cross-section taken in a plane in FIG. 2 that is perpendicular to a rod axis of an inserted rod.
Figure 4:
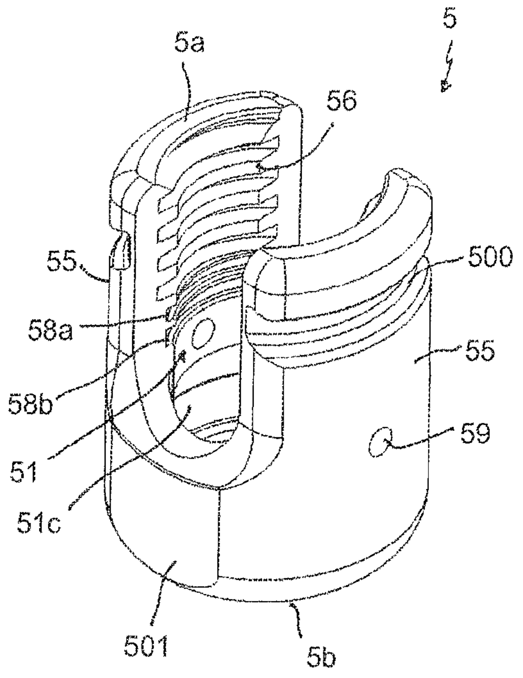
FIG. 4 shows a perspective view from above a receiving part of the coupling device of FIGS. 1 to 3.
Figure 5:
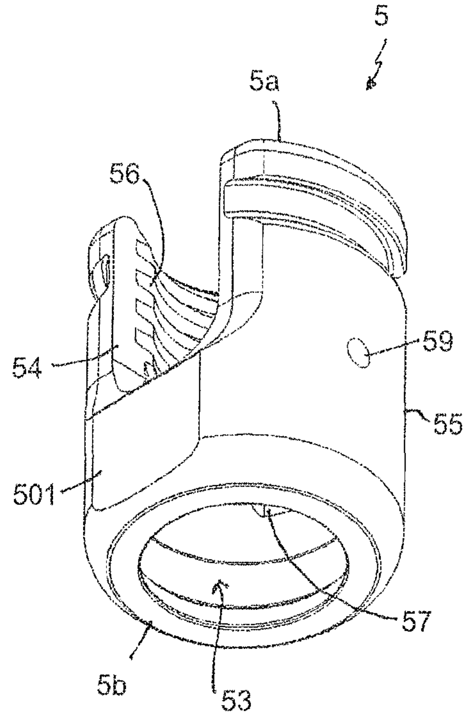
FIG. 5 shows a perspective view from below the receiving part of FIG. 4.
Figure 6:
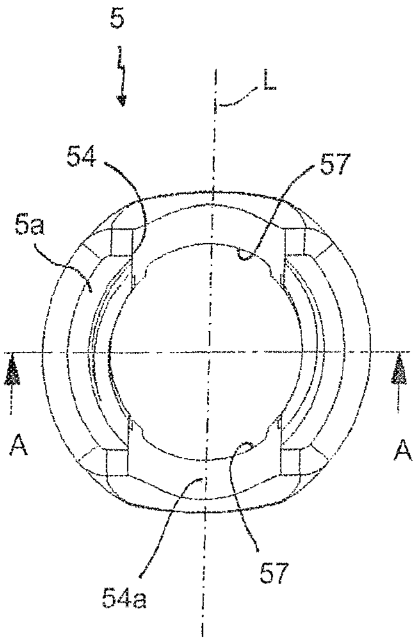
FIG. 6 shows a top view of the receiving part of FIGS. 4 and 5.

Referring to FIGS. 1 to 3, the bone anchoring device includes a bone anchoring element 1 having a shank 2 for anchoring in bone or in a vertebra and a head 3. The shank 2 has a bone engagement feature, such as a thread. The head 3 is shaped as a segment of a sphere, thus having a spherically-shaped outer surface portion. The spherically-shaped outer surface portion may include a region with a greatest outer diameter of the head 3. In addition, the head 3 has at its free end an engagement portion 4 for engagement with a tool, such as a driver. Further, the bone anchoring device includes a receiving part 5 for receiving the head 3 of the bone anchoring element 1 and for receiving a rod 100 which is configured to connect several bone anchoring devices. In the receiving part 5, a pressure element 6 is provided for exerting pressure onto the head 3 of the bone anchoring element 1 and for providing support for the rod 100. The pressure element 6 may be secured by pins 7. To lock the head and the rod 100 in the receiving part 5, a locking element 8, for example, in the form of an inner screw or set screw, is provided.

Referring in addition to FIGS. 4 to 7, the receiving part 5 will be explained in greater detail. The receiving part 5 has a first or top end 5*a* and a second or bottom end 5*b* opposite to the top end 5*a*. In general, the receiving part 5 may have a substantially cylindrical outer shape with a central longitudinal axis C extending through the top end 5*a* and the bottom end 5*b*. Coaxially to the central axis C, a passage 51 is provided that extends from the top end 5*a* to the bottom end 5*b* and that forms an opening 52 at the bottom end 5*b*. At a distance from the top end 5*a*, the passage 51 widens into an accommodation space 53 that is configured to receive the head 3 and at least a portion of the pressure element 6 therein. The receiving part 5 further has a substantially U-shaped recess 54 starting at the top end 5*a* and extending in a direction towards the bottom end 5*b*. By means of the U-shaped recess 54, two free legs 55 are formed and define a channel that is open towards the first end 5*a* for receiving the rod 100. On an inner surface of the legs 55, an internal thread 56 is formed, which in the exemplary embodiment is a square thread or another flat thread.

Figure 7:
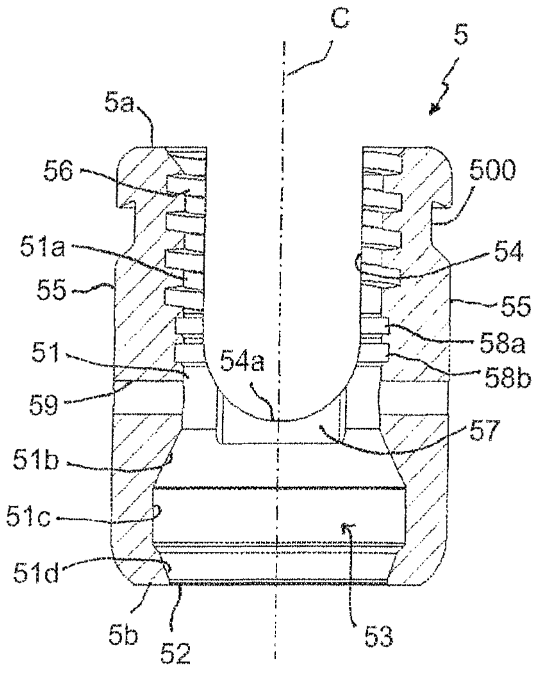
FIG. 7 shows a cross-sectional view of the receiving part of FIGS. 4 to 6, the cross-section taken along line A-A in FIG. 6.
Figure 8:
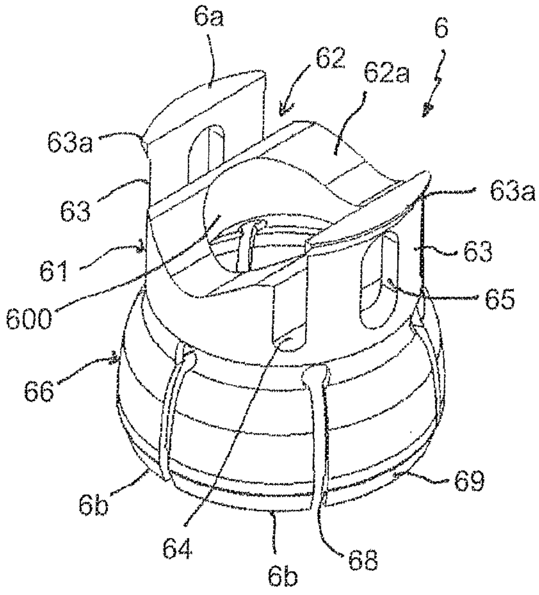
FIG. 8 shows a perspective view from above a pressure element of the coupling device of FIGS. 1 to 3.
Figure 9:
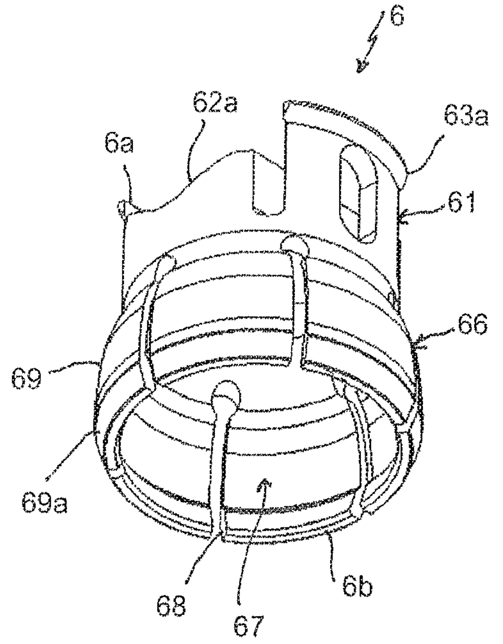
FIG. 9 shows a perspective view from below the pressure element of FIG. 8.
Figure 10:
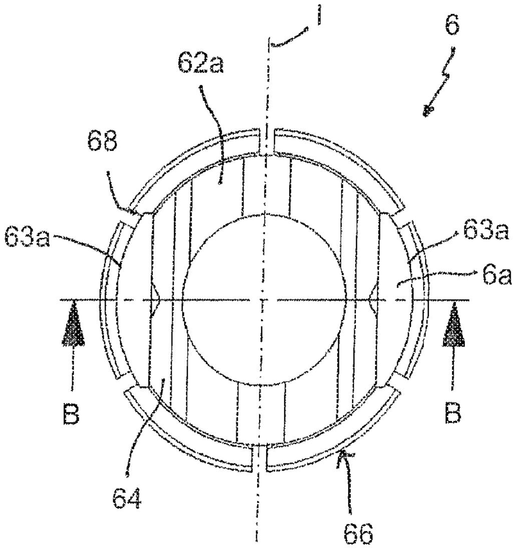
FIG. 10 shows a top view of the pressure element of FIGS. 8 and 9.

As can be seen in particular in FIG. 7, a portion of the passage 51 starting from the top end 5*a* is formed by a substantially cylindrical bore 51*a*, with an inner diameter that is smaller than a greatest outer diameter of the head 3. In particular, the greatest outer diameter of the head 3 may be the same or may be greater than a core diameter of the internal thread 56. The bore 51*a* of the passage 51 may extend below the bottom 54*a* of the U-shaped recess 54 in an axial direction. Following the bore 51*a*, the passage widens at a widening portion 51*b* into a substantially cylindrical portion 51*c* that has an inner diameter that is greater than a greatest outer diameter of the head 3 and greater than an outer diameter of the pressure element 6 that is holding the inserted head 3. Following the cylindrical section 51*c*, the passage 51 narrows towards the bottom end 5*b* in a narrowing portion 51*d*, for example, a conically narrowing portion. The width of the opening 52 may be greater than the greatest outer diameter of the head 3, such that the head 3 may be inserted from the bottom end 5*b* into the accommodation space 53. To enable the insertion of the head 3 from the bottom end 5*b* when the pressure element 6 is in the receiving part 5, the widths of the portions of the accommodation space 53 are such that the pressure element 6 can expand therein to permit the insertion of the head 3.

In the direction of the longitudinal axis L of the channel formed by the U-shaped recess 54, two opposite cutouts 57 are formed in the inner wall of the passage 51. The cutouts 57 may have a width in the circumferential direction such that a portion of the pressure element can extend therein and may be guided by the cutouts 57. In the axial direction, the cutouts 57 extend from a distance above the bottom 54*a* of the U-shaped recess 54 into the widening section 51*b* of the passage 51. An inner contour of the cutouts 57 may be adapted to the outer contour of a portion of the pressure element, as described in greater detail below. A depth of the cutouts 57 in the radial direction is at least large enough to receive a portion of the pressure element therein. The cutouts 57 thus form radially enlarged sections that serve for permitting the insertion of the pressure element 6 from the bottom end 5*b* in a first rotational orientation relative to the receiving part 5.

A circumferential first groove 58*a* may be provided at the inner wall of the legs 55 at a distance from the bottom 54*a* of the U-shaped recess 54. The first inner groove 58*a* may provide a stop for restricting an upward movement of the pressure element 6 towards the top end 5*a* when the pressure element 6 is assembled with the receiving part 5 at an insertion position. Between the circumferential first groove 58*a* and the bottom of the U-shaped recess 54*a* in the axial direction, there may be a circumferential second groove 58*b* for engagement with a portion of the pressure element 6 to secure a pre-locking position of the pressure element 6 in the receiving part.

The receiving part 5 may further include two transverse holes 59 that extend completely through the legs 55, respectively, in a direction perpendicular to the central axis C and at a circumferential position approximately at the center of each of the legs 55. The through holes 59 may serve for accommodating the pins 7, as shown in FIGS. 1 to 3. The pins 7 are configured to engage the pressure element to secure the pressure element 6 against rotation. In addition, the pins 7 may limit an upward movement of the pressure element 6.

Moreover, in the outer surface of each of the legs, at a distance from the top end 5*a*, circumferential tool engagement grooves 500 may be formed for engagement with a tool or an instrument.

At an outer surface of the receiving part 5, aligned with the U-shaped recess, two opposite flat areas 501 may be provided that reduce an overall width of the receiving part.

Referring further to FIGS. 8 to 11*b*, the pressure element 6 will be described. Preferably, the pressure element 6 is a monolithic piece which is configured to be arranged in the passage 51 and to encompass the head laterally and from a free end of the head, to exert pressure onto the head when the head 3 and the pressure element 6 are in the receiving part 5, such that the head 3 is pivotable with respect to the receiving part 5 and can be locked at an angle relative to the receiving part. In greater detail, the pressure element 6 has a first or top end 6*a* and a second or bottom end 6*b*. Adjacent to the top end, the pressure element has a first portion 61 with a substantially cylindrical outer surface, with an outer diameter that allows the pressure element 6 to move axially within the bore 51*a* of the passage 51 of the receiving part 5. At the top end 6*a*, a rod receiving recess 62 forms a rod support surface 62*a*. The rod support surface 62*a* may have a substantially V-shaped cross-section, with a longitudinal axis I extending substantially perpendicular to a cylinder axis of the first portion 61, where the cylinder axis is configured to coincide with the central axis C of the receiving part 5 when the pressure element 6 is in the receiving part 5. The depth of the rod receiving recess 62 may be smaller than a diameter of the rod 100. Hence, when the rod 100 rests on the rod support surface 62*a*, the rod 100 projects over the top end 6*a* of the pressure element, as shown, for example, in FIG. 3. The V-shape of the rod support surface 62*a* more easily facilitates use of rods with different diameters.

The rod receiving recess 62 is shaped such that two free upstanding legs 63 are formed that may be spaced apart from the rod support surface 62*a* on each side by a groove 64. By means of this, the legs 63 are slightly flexible in a direction transverse to the longitudinal axis I of the rod support surface 62*a*. A free end of each of the legs 63 may have a radially outwardly protruding rim 63*a*, an upper surface of which forms the top end 6*a* of the pressure element 6. The outwardly protruding rim 63*a* is configured to engage the respective cutouts 57 of the receiving part 5, and may be guided therein. To secure an insertion position of the pressure element, the radially outwardly protruding rim 63*a* is configured to engage the first groove 58*a* provided at the inner surface of the legs 55 of the receiving part 5. Thus, the first groove 58*a* of the receiving part forms a first securing portion and the radially outwardly projecting rims 63*a* of the pressure element forms a second securing portion configured to cooperate with the first securing portion, as explained in greater detail below. To secure a pre-locking position of the pressure element 6 in the receiving part 5, the radially outwardly protruding rim 63*a* is configured to engage the second groove 58*b* provided at the inner surface of the legs 55.

At the center of each of the legs 63 in a circumferential direction, an axially extending elongate through hole 65 is provided, that serves for receiving the pins 7 as shown in FIG. 3.

A second portion 66 of the pressure element 6 has a substantially cap-like shape that is configured to receive the head 3 of the bone anchoring element 1. The second portion 66 of the pressure element has a hollow head receiving portion 67, with an opening at the bottom end 6*b* for inserting the head 3. The head receiving portion 67 may have, lower and, upper substantially spherical sections 67*a*, 67*b*, that are shaped so as to matingly receive the spherical head 3. An intermediate section 67*c* may have a greater inner diameter for facilitating the insertion of the head 3. In addition, a plurality of axial slits 68 are formed that are open at the second end 6*b* and may have an enlarged, preferably rounded, end portion. The slits 68 extend along an axial length that covers at least the intermediate section 67*c* that has the greatest inner diameter. In general, the number, shape, and size of the slits are selected such that a desired flexibility is achieved that allows expansion of the head receiving portion 67 when the head 3 is inserted through the bottom end 6*b*, and compression around an inserted head 3. The size of the head receiving portion 67 may also be such that the head 3 can be held therein by friction prior to final locking of the head 3 in the receiving part 5.

An outer surface 69 of the second portion 66 of the pressure element 6 may be rounded, and may have a greater outer diameter than the outer diameter of the cylindrical first section 61. Adjacent to the bottom end 6*b*, the outer surface 69 includes a narrowing portion 69*a*, for example, a conically narrowing portion, that is configured to engage the narrowing portion 51*d* at the bottom region of the accommodation space 53 of the receiving part 5. When the pressure element 6 and the head 3 of the bone anchoring element 1 are in the receiving part 5 and the narrowing portion 69*a* engages the narrowing portion 51*d* of the accommodation space, the head 3 is prevented from being removed through the lower opening 52 of the receiving part.

The pressure element 6 further defines a coaxial opening or bore 600 that allows access to the tool engagement recess 4 of an inserted head 3 with a tool, such as a driver.

Figure 11A:
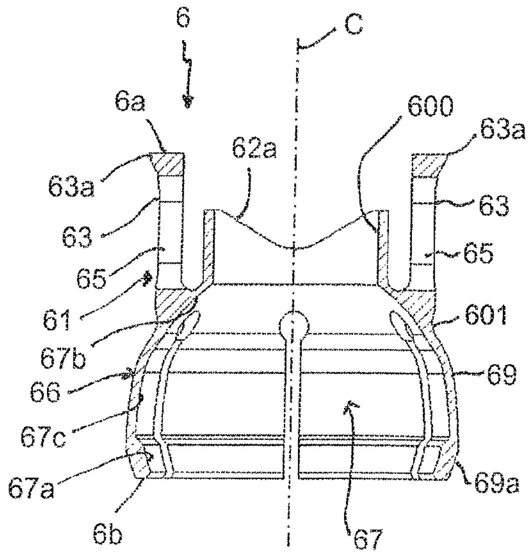
FIG. 11*a* shows a cross-sectional view of the pressure element of FIGS. 8 to 10, the cross-section taken along line B-B in FIG. 10.
Figure 11B:
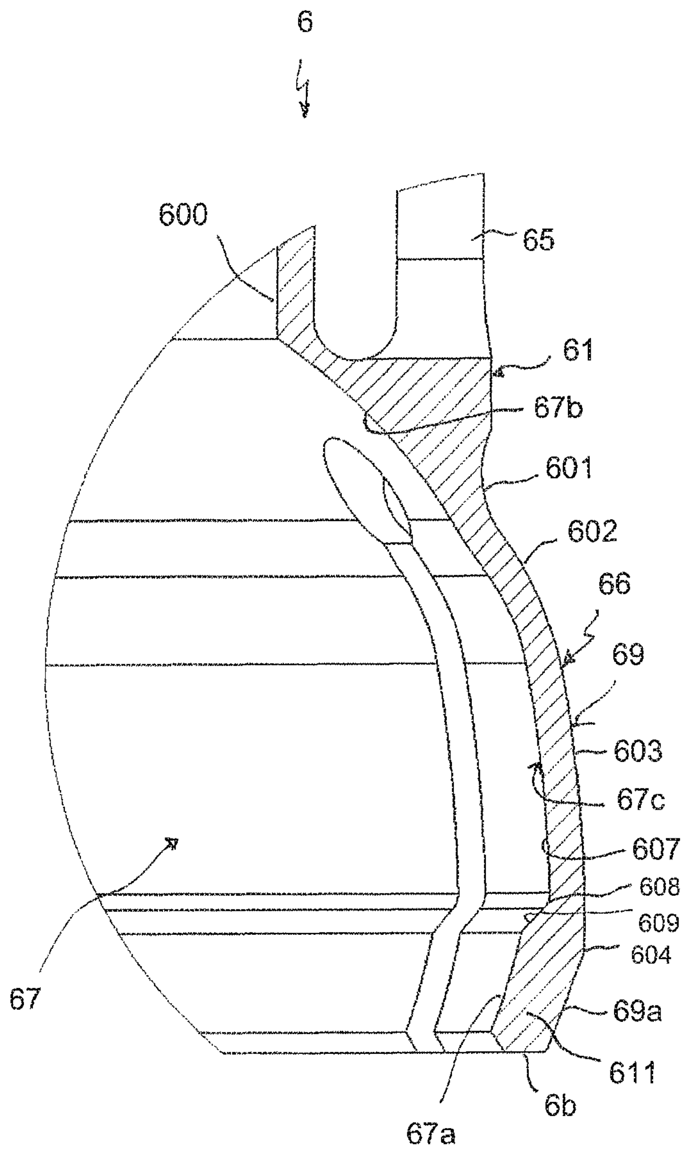
FIG. 11*b* shows an enlarged portion of FIG. 11*a*.

As can be seen in FIG. 11*a* and in an enlarged view in FIG. 11*b*, the second portion 66 of the pressure element has at its outer surface, between the outer surface 69 and the cylindrical first section 61, a groove 601 preferably extending fully circumferentially. The groove 601 forms a transition between the first section 61 and the outer surface 69 of the second section 66 of the pressure element 6. The circumferential groove 601 has a smallest diameter in a direction perpendicular to the central axis C that is smaller than the outer diameter of the cylindrical first section 61 and smaller than an outer diameter of the outer surface 69. A contour of the groove 601 may be spherical or circular in a cross-sectional view, shown in FIGS. 11*a* and 11*b*. The outer surface 69 may have, adjacent to the groove 601, a first outer surface portion 602, preferably a spherical portion with a first radius, which protrudes farther radially outward than the cylindrical first section 61. The outer surface 69 continues from the first outer surface portion 602 into a second outer surface portion 603, preferably also a spherical portion with a second radius that is greater than the first radius, and extends to an edge 604 between the second outer surface portion 603 and the narrowing portion 69*a*. The edge 604 may form the greatest outer diameter of the second portion 66 of the pressure element.

The intermediate section 67*c* of the inner surface of the head receiving portion 67, which is between the upper and lower spherical sections 67*b*, 67*a*, has a first portion 607 that widens from the upper spherical section 67*b* towards the bottom end 6*b* to a position 608 with a greatest inner diameter of the head receiving portion 67. Adjacent thereto, the intermediate section 67*c* has a second portion 609 that narrows towards the lower spherical section 67*a*, preferably in a conical shape. By means of this, there is a gap 610 formed between an inserted head 3 and the inner wall of the head receiving portion 67 in the region of the intermediate section 67*c*, as shown for example in FIG. 3. It shall be noted that the pressure element 6 has a wall portion 611 adjacent to the bottom end 6*b* which has an increased radial thickness due to the narrowing second portion 609 of the intermediate section 67*c*. This may result in an increased clamping force for clamping the head 3.

When the bone anchoring element has an enlarged head 3 that is insertable only from the bottom end 5*b* into the receiving part, the head receiving portion 67 of the pressure element must be large and flexible enough permit insertion and accommodation of such an enlarged head. With the groove 601 and the shape of the inner and outer surfaces of the second portion 66 of the pressure element, a sufficient flexibility may be achieved that allows the second portion 66 of the pressure element to spread when the head 3 is inserted. In addition, the mounting of the pressure element 6 in the receiving part 5 may also be more easily facilitated.

The parts and portions of the bone anchoring device may be made of any material, preferably, however, of titanium or stainless steel, or of a bio-compatible metal or metal alloy or plastic material. For bio-compatible alloys, a NiTi alloy, for example, Nitinol, may be used. Other materials that can be used are, for example, magnesium or magnesium alloys. Bio-compatible plastic materials include, for example, polyether ether ketone (PEEK) or poly-L-lactide acid (PLLA). The parts can be made of the same or of different materials from one another.

Figure 12:
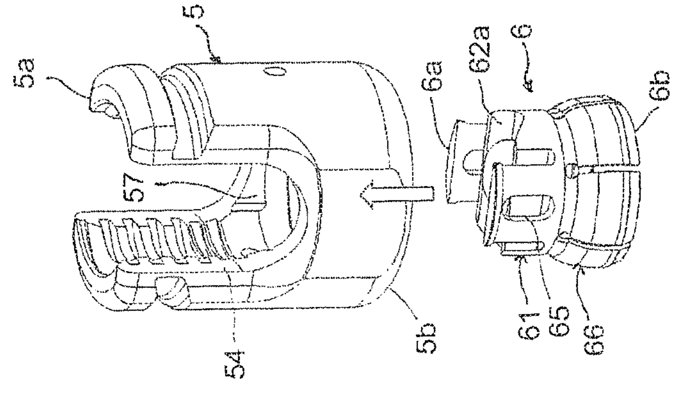
FIGS. 12 to 15 show perspective views of steps of assembling the receiving part and the pressure element of the coupling device of FIGS. 1 to 3.

Referring to FIGS. 12 to 15, steps of assembling the coupling device, i.e., the receiving part 5 with the pressure element 6, are shown. As depicted in FIG. 12, first, the pressure element 6 is oriented with its top end 6*a* facing towards the bottom end 5*b* of the receiving part 5 so that the pressure element 6 can be inserted from the bottom end 5*b* of the receiving part 5. The pressure element 6 assumes a first rotational orientation with respect to the receiving part 5 where the longitudinal axis of the rod support surface 62*a* of the pressure element 6 and the longitudinal axis of the U-shaped recess 54 for receiving the rod are perpendicular to one another.

Figure 13:
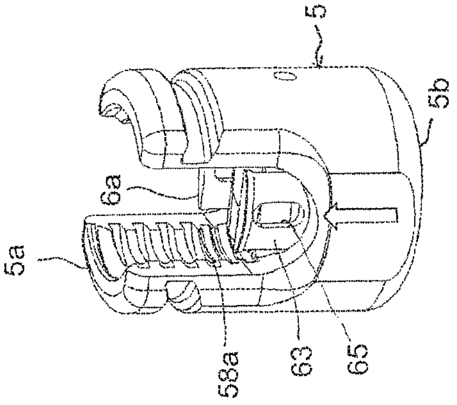

Next, as shown in FIG. 13, the pressure element 6 is inserted into the receiving part 5 through the bottom end 5*b* while at the first rotational orientation. During insertion, the outer rim 63*a* extends into the cutouts 57, which guide the pressure element 6 during insertion. The pressure element 6 is inserted up to an axial position where the rim 63*a* on each leg 63 of the pressure element 6 has moved out of the cutout 57 and is at the same axial height of the first groove 58*a*. The elongate recesses 65 may be positioned axially higher than the bottom 54*a* of the U-shaped recess, to an extent such that the elongate recesses 65 are high enough to be engaged by the pins 7. Since the outer rim 63*a* extends axially out of the cutouts 57 once the pressure element 6 is fully inserted, the pressure element can be rotated.

Figure 14:
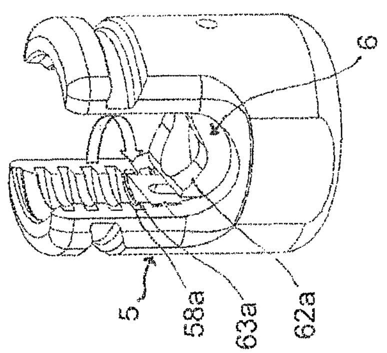

Thereafter, as shown in FIG. 14, the pressure element 6 is rotated so that the pressure element assumes a second rotational orientation where the longitudinal axis of the rod support surface 62*a* is aligned with the channel provided by the U-shaped recess 54. At the second rotational orientation, the outer rim 63*a* of the pressure element 6 engages with the upper wall of the first groove 58*a*, so that the pressure element is prevented from moving further towards the top end 5*a* of the receiving part 5 when the head 3 is inserted into the head receiving portion 67 of the pressure element 6. Thus, the upper groove 58*a* forms the first securing portion and the outer rim 63*a* forms the second securing portion that secure the pressure element 6 in the receiving part 5 at the insertion position during insertion of the head 3. As also shown in FIG. 14, the rod support surface 62*a* projects above the bottom 54*a* of the U-shaped recess 54.

Figure 15:
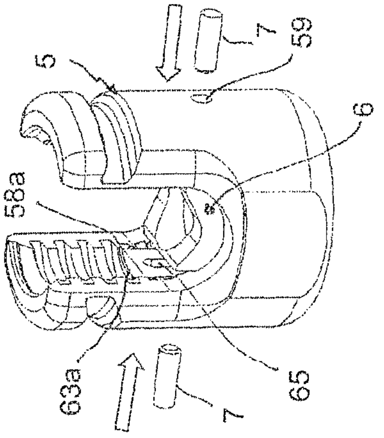

Next, as shown in FIG. 15, the pressure element 6 is secured against inadvertent rotation by means of the pins 7 that are inserted into the pin holes 59. The pins 7 have a length such that they extend into the elongate recess 65. However, it may be possible to omit the pins 7, for example, when the first portion 61 of the pressure element 6 has a size such that the pressure element is secured in the portion 51*a* of the passage 51 by friction.

Usually, the coupling device is pre-assembled. In clinical use, the bone anchoring device can be used in a first manner where the bone anchoring element 1 is pre-assembled with the coupling device including the receiving part 5 and the pressure element 6 outside a patient's body, or alternatively in a second manner where the bone anchoring element 1 is already inserted in bone or in a vertebra, and the coupling device is mounted in-situ onto the head 3 of the bone anchoring element.

Figures 16, 17, 18, 19:
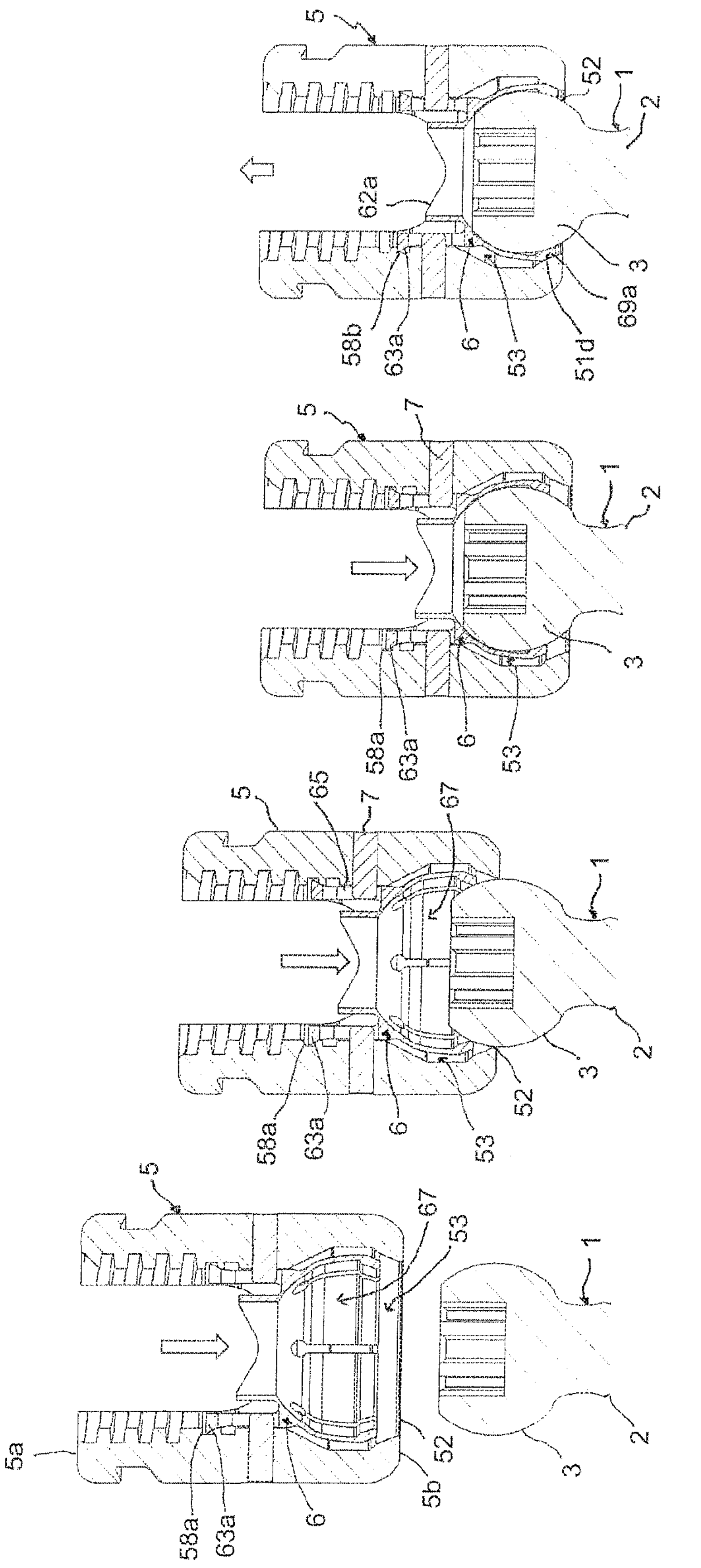
FIGS. 16 to 19 show cross-sectional views of steps of assembling the polyaxial bone anchoring device of FIGS. 1 to 3, the cross-section taken in a plane perpendicular to an axis of a channel for the rod.

With reference to FIGS. 16 to 19, the mounting of the coupling device to the bone anchoring element is described. As shown in FIG. 16, the pressure element 6 is at the insertion position where the rim 63*a* is in the first groove 58*a* and the flexible second portion 66 of the pressure element is located in the widened sections 51*b* and 51*c* of the accommodation space 53.

As shown in FIG. 17, the coupling device is placed onto the head 3 of the bone anchoring element, so that the head 3 enters through the lower opening 52 into the accommodation space 53 of the receiving part 5 and into the head receiving portion 67 of the pressure element 6. The pressure element 6 is prevented from moving towards the top end 5*a* of the receiving part, since the top end 6*a* of the outer rim 63*a* abuts against the upper wall of the first groove 58*a*. Thus, the pressure element 6 is secured at the insertion position.

Next, as shown in FIG. 18, the pressure element 6 is pressed downward. As shown in FIG. 19, since the legs 63 of the pressure element 6 are slightly flexible, the outer rim 63 can disengage from the first groove 58*a* when the pressure element 6 is pressed down and engage the second groove 58*b*. By pulling the receiving part 5, for example, upward, the pressure element is moved further downward relative to the receiving part 5 until the narrowing outer surface portion 69 engages the narrowing inner surface portion 51*d* of the receiving part 5. Thus, as depicted in FIG. 19, the pressure element 6 is at a pre-locking position where the lower opening 52 is reduced or partially blocked by the pressure element 6, so that the head 3 is prevented from being removed through the lower opening 52.

Due to the large outer diameter of the head 3, the bone anchoring element 1 can pivot in the receiving part to a greater maximum angle as compared to bone anchoring devices with smaller heads. For example, instead of heads with a greatest outer diameter of 7 mm, bone anchoring elements with a head of a greatest outer diameter of 8 mm can be used. The maximum pivot angle that the shank 2 can form with the central axis C may be 35° or more. Due to the large head, a stable and robust implant with increased holding force can be provided.

In use, once a desired angular position of the bone anchoring element 1 relative to the receiving part 5 has been achieved, the rod 100 is inserted and the locking element 8 is inserted and tightened to lock the head and the rod relative to the receiving part.

In clinical use, a plurality of polyaxial bone anchoring devices are inserted into bone parts or into vertebrae, in particular, into the pedicles of vertebrae. The respective coupling devices are then aligned so that the rod can be received in the rod receiving portions of two or more of the bone anchoring devices.

Modifications of the above described embodiments are also conceivable. In particular, the shape of the parts is not limited to the detailed shape shown in the figures. Deviations may be possible and are encompassed by the disclosure. For example, the first and the second securing portions may be located at other positions on the receiving part and the pressure element, and may be shaped differently. It may be sufficient to have only one first and only one second securing portion on the same side relative to the rod receiving recess.

In addition, instead of the locking member being a set screw, all other kinds of locking assemblies known in the art may be used. For the bone anchoring element, all types of bone anchoring elements suitable for anchoring in bone or in a vertebra, such as bone screws, bone nails, etc., may be used. The rod can be any elongate device that is configured to connect two bone anchoring devices. The rod may have various shapes and/or varying cross-sections along its length. The rod may be stiff or more flexible.

The spherical outer surface portion of the head may only be partly spherical when viewed in the circumferential direction, and the seat portion in the head receiving portion may be adapted thereto such that pivoting of the head is possible only in a predefined plane, for example. Other restriction structures to limit the pivoting of the bone anchoring element to one or several distinct planes may also be applied to provide such a uniplanar or otherwise limited angulating bone anchoring device.

Moreover, the head receiving portion may have a design that allows pivoting of the bone anchoring element to a greater pivot angle to one side or radial direction compared to other sides or radial directions.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A coupling device for coupling a rod to a bone anchoring element having a head and a shank, the coupling device comprising:

a monolithic receiving part having a first end, a second end below the first end, a central axis extending between the first and second ends, a passage extending from the first end towards the second end, a recess extending from the first end towards the second end and forming two free legs for receiving the rod therebetween, an accommodation space for accommodating the head of the bone anchoring element, and an opening at the second end; and a pressure element positionable at least partially in the accommodation space, the pressure element comprising a rod support surface for engaging the rod and an expandable portion configured to engage and exert pressure on the head;

wherein the pressure element is insertable through the opening at the second end into the accommodation space while at a first rotational orientation relative to the receiving part where a first engagement surface of the receiving part and a second engagement surface of the pressure element are out of circumferential alignment with one another, and wherein the pressure element is rotatable to a second rotational orientation relative to the receiving part where the first engagement surface and the second engagement surface engage one another to restrict movement of the pressure element towards the first end; and wherein when the pressure element is assembled to the receiving part, the receiving part is configured to directly engage and urge the expandable portion of the pressure element towards the head to lock the head relative to the receiving part.

2. The coupling device of claim 1, wherein the expandable portion of the pressure element is flexible and defines a hollow interior for accommodating at least a portion of the head having a greatest width of the head.

3. The coupling device of claim 2, wherein the receiving part has a narrowing portion adjacent the opening that is configured to cooperate with a corresponding narrowing portion of the pressure element to clamp the head.

4. The coupling device of claim 1, wherein when the first engagement surface and the second engagement surface are engaged, the first engagement surface forms a stop to prevent the removal of the pressure element through the first end of the receiving part.

5. The coupling device of claim 1, wherein the first engagement surface is formed by a groove, and the second engagement surface is formed by a projection on the pressure element.

6. The coupling device of claim 1, wherein the pressure element comprises two legs for receiving the rod, and wherein the second engagement surface is formed on an outer surface of at least one of the legs of the pressure element.

7. The coupling device of claim 1, wherein at least one radially enlarged section is formed in the passage that is positioned axially between the accommodation space and the first end of the receiving part that is sized to accommodate the second engagement surface of the pressure element when the pressure element is inserted into the receiving part at the first rotational orientation.

8. The coupling device of claim 7, wherein the at least one radially enlarged section is circumferentially aligned with the recess for receiving the rod.

9. The coupling device of claim 7, wherein the at least one radially enlarged section extends axially at least from a bottom of the recess for receiving the rod into an upper portion of the accommodation space.

10. The coupling device of claim 7, wherein the at least one radially enlarged section has a circumferential width that is configured to guide the second engagement surface of the pressure element therethrough during axial insertion of the pressure element into the receiving part.

11. The coupling device of claim 1, wherein at the first rotational orientation, a longitudinal axis of the rod support surface of the pressure element is arranged perpendicularly to a longitudinal axis of the recess of the receiving part.

12. The coupling device of claim 1, wherein at the second rotational orientation, a longitudinal axis of the rod support surface of the pressure element is aligned or parallel with a longitudinal axis of the recess of the receiving part.

13. The coupling device of claim 1, wherein a circumferential groove is formed in an outer surface of the pressure element at an axial position between the rod support surface and the expandable portion.

14. A bone anchoring device comprising the coupling device of claim 1, and the bone anchoring element having the head and the shank.

15. The bone anchoring device of claim 14, wherein the head of the bone anchoring element has a greatest outer width that is greater than the smallest inner width of the passage measured in a direction perpendicular to the central axis.

16. The bone anchoring device of claim 14, wherein the expandable portion of the pressure element is configured to engage a portion of the head below a greatest width of the head.

17. A bone anchoring device comprising:

a bone anchoring element comprising a head and a shank; and a coupling device for coupling a rod to the bone anchoring element, the coupling device comprising:

a receiving part having a first end, a second end below the first end, a central axis extending between the first and second ends, a passage extending from the first end towards the second end, a recess extending from the first end towards the second end and forming two free legs for receiving the rod therebetween, an accommodation space for accommodating the head of the bone anchoring element, and an opening at the second end; and a pressure element positionable at least partially in the accommodation space, the pressure element comprising a rod support surface for engaging the rod and an expandable portion configured to engage at least a portion of the head below a greatest width of the head and to exert pressure on the head, wherein an inner wall of the expandable portion comprises upper and lower portions configured to simultaneously engage the head, and an intermediate portion configured to be radially spaced apart from the head when the upper and lower portions engage the head;

wherein the pressure element is insertable through the opening at the second end into the accommodation space while at a first rotational orientation relative to the receiving part where a first engagement surface of the receiving part and a second engagement surface of the pressure element are out of circumferential alignment with one another, and wherein the pressure element is rotatable to a second rotational orientation relative to the receiving part where the first engagement surface and the second engagement surface engage one another to restrict movement of the pressure element towards the first end.

18. A method for assembling a coupling device to a bone anchoring element having a head and a shank for coupling a rod to the bone anchoring element, the coupling device comprising a monolithic receiving part having a first end, a second end below the first end, a central axis extending between the first and second ends, a passage extending from the first end towards the second end, a recess extending from the first end towards the second end and forming two free legs for receiving the rod therebetween, an accommodation space for accommodating the head of the bone anchoring element, and an opening at the second end, and a pressure element positionable at least partially in the accommodation space, the pressure element comprising a rod support surface for engaging the rod and an expandable portion configured to engage and exert pressure on the head, the method comprising:

orienting the pressure element at a first rotational orientation relative to the receiving part;

inserting the pressure element through the opening at the second end into the accommodation space while at the first rotational orientation relative to receiving part where a first engagement surface of the receiving part and a second engagement surface of the pressure element are out of circumferential alignment with one another;

rotating the pressure element to a second rotational orientation relative to the receiving part where the first engagement surface and the second engagement surface engage one another to restrict movement of the pressure element towards the first end; and adjusting the pressure element, when the head and the pressure element are assembled to the receiving part, such that the receiving part directly engages and urges the expandable portion of the pressure element towards the head to lock the head relative to the receiving part.

19. The method of claim 18, further comprising inserting the head of the bone anchoring element through the opening at the second end of the receiving part into the accommodation space.

20. A coupling device for coupling a rod to a bone anchoring element having a head and a shank, the coupling device comprising:

a monolithic receiving part having a first end, a second end below the first end, a central axis extending between the first and second ends, a recess extending from the first end towards the second end and forming two free legs for receiving the rod therebetween, an accommodation space for accommodating the head of the bone anchoring element, and an opening at the second end; and a monolithic pressure element positionable at least partially in the accommodation space, the pressure element comprising a recessed rod support surface for engaging the rod and an expandable portion configured to engage and exert pressure on at least a portion of the head below a greatest width of the head while in the accommodation space;

wherein the pressure element is insertable through the opening at the second end into the accommodation space to a position where a first engagement surface of the receiving part and a second engagement surface of the pressure element engage one another to restrict removal of the pressure element through the opening;

wherein when the pressure element is assembled to the receiving part, the receiving part is configured to directly engage and urge the expandable portion of the pressure element towards the head to lock the head relative to the receiving part; and wherein the second engagement surface of the pressure element is spaced apart from the expandable portion, and has a greatest outer width measured in a direction perpendicular to the central axis that is greater than all other portions of the pressure element located axially above a bottom of the recessed rod support surface.

* * * * *